United States Patent

Weston et al.

(10) Patent No.: US 9,352,079 B2
(45) Date of Patent: May 31, 2016

(54) SAFETY NEEDLE ACCESSORY

(75) Inventors: Terence Edward Weston, Norfolk (GB); Douglas Arthur Emmott, Suffolk (GB)

(73) Assignee: Salvus Technology Limited, Stradbroke, Suffolk (GB)

( * ) Notice: Subject to any disclaimer, the term of this patent is extended or adjusted under 35 U.S.C. 154(b) by 175 days.

(21) Appl. No.: 11/817,075

(22) PCT Filed: Feb. 15, 2006

(86) PCT No.: PCT/GB2006/000528
§ 371 (c)(1),
(2), (4) Date: Sep. 14, 2007

(87) PCT Pub. No.: WO2006/090118
PCT Pub. Date: Aug. 31, 2006

(65) Prior Publication Data
US 2008/0167624 A1    Jul. 10, 2008

(30) Foreign Application Priority Data

Feb. 25, 2005 (GB) .................................. 0504130.6
Mar. 30, 2005 (GB) .................................. 0506431.6

(51) Int. Cl.
*A61M 5/32* (2006.01)
*A61M 5/31* (2006.01)
*A61M 5/00* (2006.01)

(52) U.S. Cl.
CPC ............. *A61M 5/002* (2013.01); *A61M 5/3202* (2013.01); *A61M 5/326* (2013.01); *A61M 2005/3109* (2013.01); *A61M 2005/3268* (2013.01)

(58) Field of Classification Search
CPC . A61M 5/3232; A61M 5/3213; A61M 5/321; A61M 5/326; A61M 5/3243; A61M 5/3271
USPC ......... 604/110, 192, 197, 198, 199, 263, 240, 604/242, 243
See application file for complete search history.

(56) References Cited

U.S. PATENT DOCUMENTS 1,845,036 A    2/1932  Busher
2,677,373 A *  5/1954  Barradas ........................ 604/192
(Continued)

FOREIGN PATENT DOCUMENTS

CN    1777453 A    5/2006
EP    0467173 A1   1/1992
(Continued)

OTHER PUBLICATIONS

"seal." Merriam-Webster.com. Merriam-Webster, 2011.Web. Jul. 21, 2011.*

(Continued)

*Primary Examiner* — Kami A Bosworth
*Assistant Examiner* — Matthew A Engel
(74) *Attorney, Agent, or Firm* — Panitch Schwarze Belisario & Nadel LLP

(57) ABSTRACT

This invention relates to a safety needle accessory sealed within a pack suitable for sealing pre-filled syringes. The safety needle accessory comprises a hub for surrounding a hollow needle having a tip and having a connector for attachment to a syringe, a slidable sleeve adapted to slide over the needle in a first longitudinal direction from a first position in which the needle is fully or partially covered by the sleeve to a second position in which the needle is exposed, and in a second longitudinal direction from the second position to a third position in which the needle is fully covered by the sleeve, and a pack surrounding the hollow needle, hub and slidable sleeve having a closed end covering the needle and an open end exposing the connector of the hub. The safety needle accessory further comprises a first seal attached to the connector of the hub and a second seal between the hub and the pack.

12 Claims, 3 Drawing Sheets

(56) References Cited

U.S. PATENT DOCUMENTS

| | | | |
|---|---|---|---|
| 3,114,455 A | 12/1963 | Claisse et al. | |
| 3,134,380 A * | 5/1964 | Armao | 604/198 |
| 3,677,245 A | 7/1972 | Welch | |
| 4,553,541 A | 11/1985 | Burns | |
| 4,564,054 A * | 1/1986 | Gustavsson | A61J 1/2096 141/329 |
| 4,664,654 A * | 5/1987 | Strauss | A61M 5/326 604/198 |
| 4,735,203 A | 4/1988 | Ryder et al. | |
| 4,795,432 A * | 1/1989 | Karczmer | 604/110 |
| 4,813,940 A | 3/1989 | Parry | |
| 4,850,996 A | 7/1989 | Cree | |
| 4,892,521 A * | 1/1990 | Laico et al. | 604/192 |
| 4,911,693 A | 3/1990 | Paris | |
| 4,927,019 A | 5/1990 | Haber et al. | |
| 5,015,240 A | 5/1991 | Soproni et al. | |
| 5,051,109 A * | 9/1991 | Simon | 604/263 |
| 5,104,384 A | 4/1992 | Parry | |
| 5,219,339 A | 6/1993 | Saito | |
| 5,242,401 A | 9/1993 | Colsky | |
| 5,273,539 A | 12/1993 | Chen | |
| 5,312,366 A | 5/1994 | Vailancourt | |
| 5,336,197 A | 8/1994 | Kuracina et al. | |
| 5,385,561 A | 1/1995 | Cerny | |
| 5,421,347 A | 6/1995 | Enstrom | |
| 5,549,568 A * | 8/1996 | Shields | 604/192 |
| 5,562,624 A * | 10/1996 | Righi | A61M 5/326 604/110 |
| 5,601,535 A | 2/1997 | Byrne et al. | |
| 5,645,530 A * | 7/1997 | Boukhny et al. | 604/22 |
| 5,658,256 A * | 8/1997 | Shields | A61M 5/3202 604/192 |
| 5,669,888 A | 9/1997 | Trapp | |
| 5,755,696 A | 5/1998 | Caizza | |
| 5,810,784 A * | 9/1998 | Tamaro | A61M 5/001 128/919 |
| 5,891,103 A | 4/1999 | Burns | |
| 5,893,842 A * | 4/1999 | Imbert | 604/110 |
| 5,894,015 A * | 4/1999 | Rechtin | A61M 5/001 422/292 |
| 5,910,130 A | 6/1999 | Caizza et al. | |
| 5,944,699 A * | 8/1999 | Barrelle et al. | 604/240 |
| 5,971,966 A | 10/1999 | Lav | |
| 6,203,529 B1 | 3/2001 | Gabriel et al. | |
| 6,210,374 B1 | 4/2001 | Malencheck | |
| 6,261,264 B1 | 7/2001 | Tamaro | |
| 6,331,174 B1 | 12/2001 | Reinhard et al. | |
| 6,398,762 B1 | 6/2002 | Vetter et al. | |
| 6,511,460 B1 | 1/2003 | Arnissolle | |
| 6,537,259 B1 | 3/2003 | Niermann | |
| 6,565,541 B2 * | 5/2003 | Sharp | 604/192 |
| 6,685,676 B2 | 2/2004 | Jansen et al. | |
| 7,041,086 B2 | 5/2006 | Yang | |
| 7,182,734 B2 | 2/2007 | Saulenas et al. | |
| 7,223,258 B2 | 5/2007 | Crawford | |
| 7,713,280 B2 | 5/2010 | Marshall et al. | |
| 8,105,293 B2 * | 1/2012 | Pickhard | A61M 5/322 604/110 |
| 8,425,468 B2 * | 4/2013 | Weston | A61M 5/002 604/110 |
| 8,979,802 B2 * | 3/2015 | Woehr | A61M 24/0618 604/164.08 |
| 2002/0004648 A1 | 1/2002 | Larsen et al. | |
| 2002/0087180 A1 | 7/2002 | Searle et al. | |
| 2003/0014018 A1 * | 1/2003 | Giambattista et al. | 604/198 |
| 2003/0144633 A1 | 7/2003 | Kirchhofer | |
| 2004/0049160 A1 * | 3/2004 | Hsieh et al. | 604/195 |
| 2004/0082911 A1 * | 4/2004 | Tiu et al. | 604/110 |
| 2004/0116877 A1 * | 6/2004 | Yang | 604/263 |
| 2004/0210196 A1 * | 10/2004 | Bush Jr. | A61M 5/32 604/192 |
| 2005/0038391 A1 * | 2/2005 | Wittland | A61L 2/20 604/192 |
| 2006/0129173 A1 | 6/2006 | Wilkinson | |
| 2006/0167411 A1 | 7/2006 | Weston et al. | |
| 2008/0183140 A1 | 7/2008 | Paproski et al. | |
| 2008/0215013 A1 * | 9/2008 | Felix-Faure | 604/192 |
| 2009/0012478 A1 * | 1/2009 | Weston | 604/192 |
| 2010/0076382 A1 * | 3/2010 | Weston | A61M 5/002 604/198 |
| 2013/0190693 A1 * | 7/2013 | Ekman et al. | 604/192 |

FOREIGN PATENT DOCUMENTS

| | | |
|---|---|---|
| EP | 0744183 B1 | 11/1996 |
| EP | 0815884 A | 1/1998 |
| EP | 1252907 A1 | 10/2002 |
| EP | 1447108 A1 | 8/2004 |
| EP | 1535640 A1 | 6/2005 |
| EP | 1558311 A1 | 8/2005 |
| FR | 2701848 A | 9/1994 |
| JP | 3158171 A | 7/1991 |
| WO | 9111212 A1 | 8/1991 |
| WO | WO 9400172 A1 * | 1/1994 ............ A61M 5/32 |
| WO | 9419036 A1 | 9/1994 |
| WO | 0176665 A1 | 10/2001 |
| WO | 0191837 A1 | 12/2001 |
| WO | 02089878 A1 | 11/2002 |
| WO | 02100467 A2 | 12/2002 |
| WO | 03066141 A1 | 8/2003 |
| WO | 2004000397 A1 | 12/2003 |
| WO | 2004/071560 A | 8/2004 |
| WO | 2004069302 A2 | 8/2004 |
| WO | 2006082350 A1 | 8/2006 |
| WO | 2006090118 A1 | 8/2006 |
| WO | 2008067467 A2 | 6/2008 |

OTHER PUBLICATIONS

Definition of 'Contact' —Collins English Dictionary. Accessed online Jan. 15, 2014.*

Chinese Office Action for the corresponding Chinese Patent Application No. 200680006138.6; dated Jun. 5, 2009; 8 pages (including English translation).

European Search Report issued on Oct. 4, 2010 in European Patent Application No. EP 09 17 5295.

Office Action issued Dec. 7, 2010 in U.S. Appl. No. 12/470,220.

Australian Examination Report for the related Australian Application No. 2004212245 dated Nov. 11, 2008.

Chinese Office Action for the related Chinese Application No. 200480006925.1 dated Feb. 20, 2009.

Chinese Office Action for the related Chinese Application No. 200480006925.1 dated Jul. 10, 2009.

Chinese Office Action for the related Chinese Application No. 200480006925.1 dated Dec. 28, 2007.

Chinese Office Action for the related Chinese Application No. 2005800477077 dated Sep. 25, 2009.

Chinese Office Action for the related Chinese Application No. 200680006138.6 dated Dec. 11, 2009.

European Search Report for the related European Application No. 03 25 7489 dated May 25, 2004.

European Search Report for the related European Application No. 03 25 2192 dated May 26, 2003.

U.K. Search Report for the related U.K. Application No. 0621157.7 dated Jan. 25, 2007.

International Search Report and Written Opinion for the related International Application No. PCT/GB2005/000357 dated Aug. 26, 2005.

International Search Report and Written Opinion for the related International Application No. PCT/US2007/017455 dated Nov. 19, 2007.

International Search Report and Written Opinion for the related International Application No. PCT/GB2004/000516 dated May 27, 2004.

Japanese Office Action for the related Japanese Application No. 2006-502257 dated Sep. 11, 2009.

Japanese Office Action for the related Japanese Application No. 2006-502257 dated Jan. 15, 2010.

Office Action for the related U.S. Appl. No. 10/545,160, dated Mar. 3, 2010.

(56) References Cited

OTHER PUBLICATIONS

Office Action for the related U.S. Appl. No. 11/815,475, dated Oct. 1, 2008.
Office Action for the related U.S. Appl. No. 11/815,475, dated Jan. 4, 2010.
Office Action for the related U.S. Appl. No. 11/815,475, dated Apr. 9, 2009.
Office Action for the related U.S. Appl. No. 10/545,160, dated Aug. 18, 2009.
Office Action for the related U.S. Appl. No. 11/815,475, dated Aug. 21, 2009.
International Search Report and Written Opinion for the related International Application No. PCT/US2008/077352 mailed Jan. 30, 2009.
Partial European Search Report for the related European Application No. 09175295.6 dated Apr. 9, 2010.
Chinese Office Action for the related Chinese Application No. 200680006138.6 dated Apr. 15, 2010.
International Preliminary Report on Patentability for the related International Application No. PCT1US20081077352 dated Apr. 13, 2010.
Office Action issued Jul. 30, 2010 in Chinese Application No. 20068006138.6.
Office Action Issued Sep. 7, 2010 in Japanese Patent Application No. 2007-553675.
Office Action Issued Oct. 6, 2011 in U.S. Appl. No. 10/545,160.
Office Action Issued Apr. 29, 2011 in U.S. Appl. No. 12/276,679.
Office Action Issued May 6, 2011 in U.S. Appl. No. 12/470,220.
Office Action issued Apr. 26, 2011 in JP Application No. 2007-556647.
Office Action issued Jun. 17, 2011 in U.S. Appl. No. 12/680,811.
Office Action issued Sep. 23, 2011 in CN Application No. 200880110889.1.
Office Action issued Dec. 23, 2011 in U.S Appl. No. 12/276,679.
Office Action issued Jan. 5, 2012 in U.S Appl. No. 121680,811.
Witness statement of T. E. Weston (inventor), Aug. 27, 2010.
Second witness statement of T. E. Weston (inventor), Mar. 24, 2011.
Third witness statement of T. E. Weston (inventor), Jan. 5, 2012.
Witness statement of John Davison, May 3, 2011.
Statement from claimant in UK revocation proceeding regarding EP Patent No. 1558311, Jul. 15, 2010.
Defendant's counter-statement in UK revocation proceeding regarding EP Patent No. 1558311, Aug. 31, 2010.
Defendant's supplementary counter-statement in UK revocation proceeding regarding EP Patent No. 1558311, Mar. 25, 2011.
Written Preliminary Evaluation in UK revocation proceeding regarding EP Patent No. 1558311, Nov. 10, 2011.
Witness statement of Barry Peter Liversidge on behalf of tip-top.com Ltd. in UK revocation proceeding regarding EP Patent No. 1558311, Jan. 19, 2012.
Defendant's further counter-statement in UK revocation proceeding regarding EP Patent No. 1558311, Jan. 17, 2012.
Defendant's consolidated counter-statement in UK revocation proceeding regarding EP Patent No. 1558311, Mar. 9, 2012.
Office Action issued Aug. 1, 2012 in U.S. Appl. No. 12/680,811.
Office Action issued Dec. 5, 2012 in U.S. Appl. No. 12/276,679.
Office Action issued Jan. 16, 2014 in U.S. Appl. No. 12/470,220, by Emmott.

\* cited by examiner

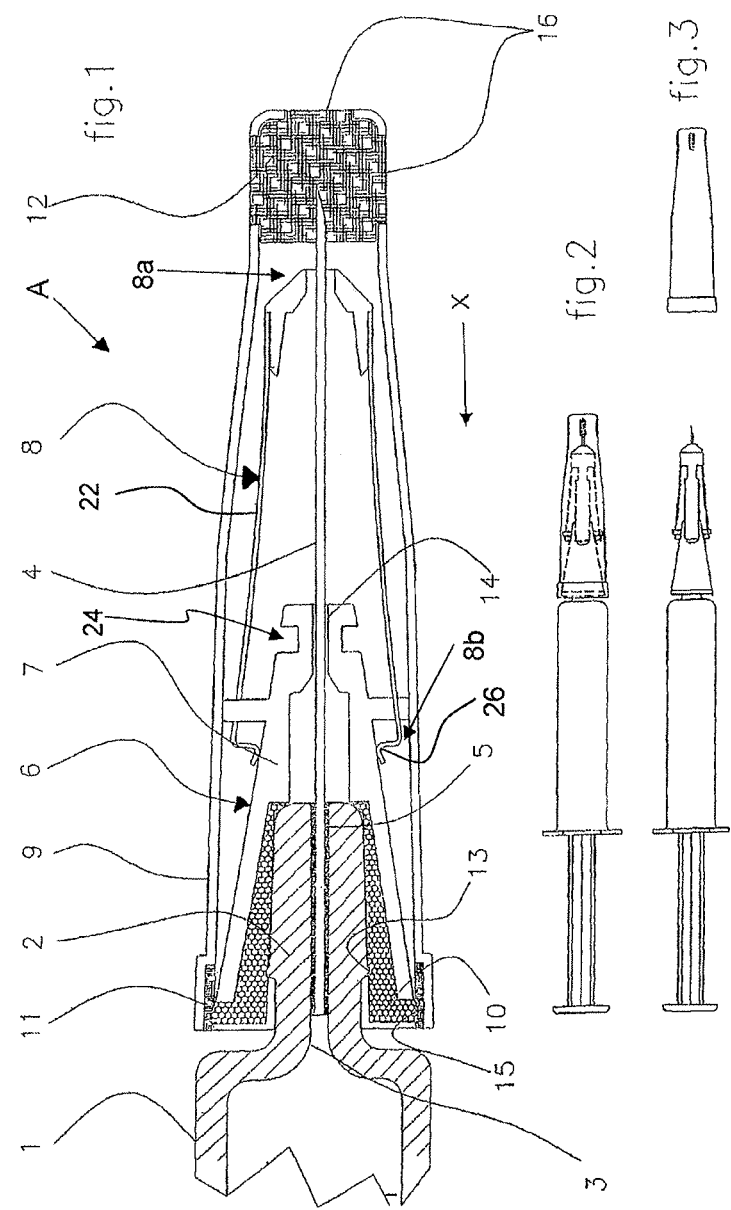

SAFETY NEEDLE ACCESSORY

CROSS-REFERENCE TO RELATED APPLICATIONS

This application is a Section 371 of International Application No. PCT/GB2005/000528, filed Feb. 15, 2006, which was published in the English language on Aug. 31, 2006, under International Publication No. WO 2006/090118 A1 and the disclosure of which is incorporated herein by reference.

BACKGROUND OF THE INVENTION

This invention relates to a safety needle accessory and particularly to a safety needle accessory sealed with in a pack suitable for sealing pre-filled syringes.

Needle stick injuries carry a significant risk of spreading infection such as HIV and hepatitis, and are commonplace among healthcare workers. The USA has led the way in introducing legislation that obliges healthcare providers to use the safest devices when giving injections, intravenous drug administration and similar invasive procedures. Other countries are following, and even without legislation, the ever-present risk of litigation has alerted pharmaceutical companies and health authorities to seek suitable safe devices.

As a result of the heightened awareness of needle stick injuries, there have been a large number of inventions purporting to solve the problem. Most take the form of a protective sleeve which covers the needle tip after the injection has been given, or means for retracting the needle rapidly into the syringe barrel. In the former case, a weakness of the designs has been the need for the user to perform an action to render the needle safe; thus if the step is omitted, the risk remains. In the second case, the needle retraction mechanism requires that the syringe plunger is pushed to the end of its stroke in order to activate the retraction mechanism. In other words, virtually none of the devices are "fail safe". In many real-life situations, the patient can involuntarily react to the pain of the injection and pull away from the needle, exposing the sharp tip, and therefore presenting a risk of a needle stick.

Another drawback of prior art safety needles (which in the present context includes safety syringes) is that they are not compatible with current accepted practice. The problems includes drug incompatibility with the device construction materials, difficulty in using standard sterilizing methods, difficulty in fitting to the syringe, large size, difficulty in filling, and very high cost.

A common requirement is for pre-filled syringes, and for reasons of drug compatibility and long-term storage, the syringe barrel is often made from glass, with the hypodermic needle bonded into the delivery end of the syringe barrel. Alternatively, a few drugs are compatible with plastics, and there are available plastic syringe barrels with molded or bonded hypodermic needles. Hitherto, there have not been any successful combinations of pre-filled syringe with a bonded-in needle and a safety device to protect the user from suffering a needle-stick injury, and it is to this requirement the present invention is directed. One of the main reasons for the lack of commercial success is that the proposed new devices often include drug contact materials which do not have a safety and compatibility record, or have clumsy operating procedure, are too big, or incompatible with common filling techniques and so forth.

As stated hereinabove, there have been no successful safety needle and pre-filled syringe combinations, and the challenge is to meet the strict requirements of various sterilizing methods, maintaining sterility of the drug and needle during storage, preventing loss of drug through thermal expansion, ease of use, and low cost.

BRIEF SUMMARY OF THE INVENTION

Accordingly, the present invention provides a safety needle accessory comprising a hub for surrounding a hollow needle having a tip and having a connector for attachment to a syringe, a slidable sleeve adapted to slide over the needle in a first longitudinal direction from a first position in which the needle is fully or partially covered by the sleeve to a second position in which the needle is exposed, and in a second longitudinal direction from the second position to a third position in which the needle is fully covered by the sleeve, and a pack surrounding the hollow needle, hub and slidable sleeve having a closed end covering the needle and an open end exposing the connector of the hub, wherein the safety needle accessory further comprises a first seal attached to the connector of the hub and a second seal between the hub and the pack.

The present invention also provides an injection device comprising a syringe having a hollow needle attached thereto and a safety needle accessory as defined herein.

In a first preferred embodiment, a safety device as described in our co-pending patent application WO 2004/071560 is assembled to a syringe (i.e. barrel and plunger) having a bonded hypodermic needle, over which is fitted the safety device. A seal between the syringe and hub of the safety needle accessory is provided by a soft polymer. A pack encloses the syringe and safety device assembly, and has a rubber seal which seals against the periphery of the safety device hub, and further has a rubber seal which seals the opening of the hypodermic needle.

In a second preferred embodiment, which is similar to the first, the seal between the hub of the safety needle accessory and connector also seals directly to the pack, and the hypodermic needle seal is provided as before.

As an alternative to the previous embodiments, in a third embodiment, the safety device is bonded to the outlet connector of a syringe.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 1 shows a longitudinal section on the centreline of a syringe and safety needle accessory in accordance with an embodiment of the present invention;

FIGS. 2 and 3 show an overall view of the syringe and safety needle accessory in accordance with the present invention with the pack attached and detached, respectively;

DETAILED DESCRIPTION OF THE INVENTION

Figure 4:
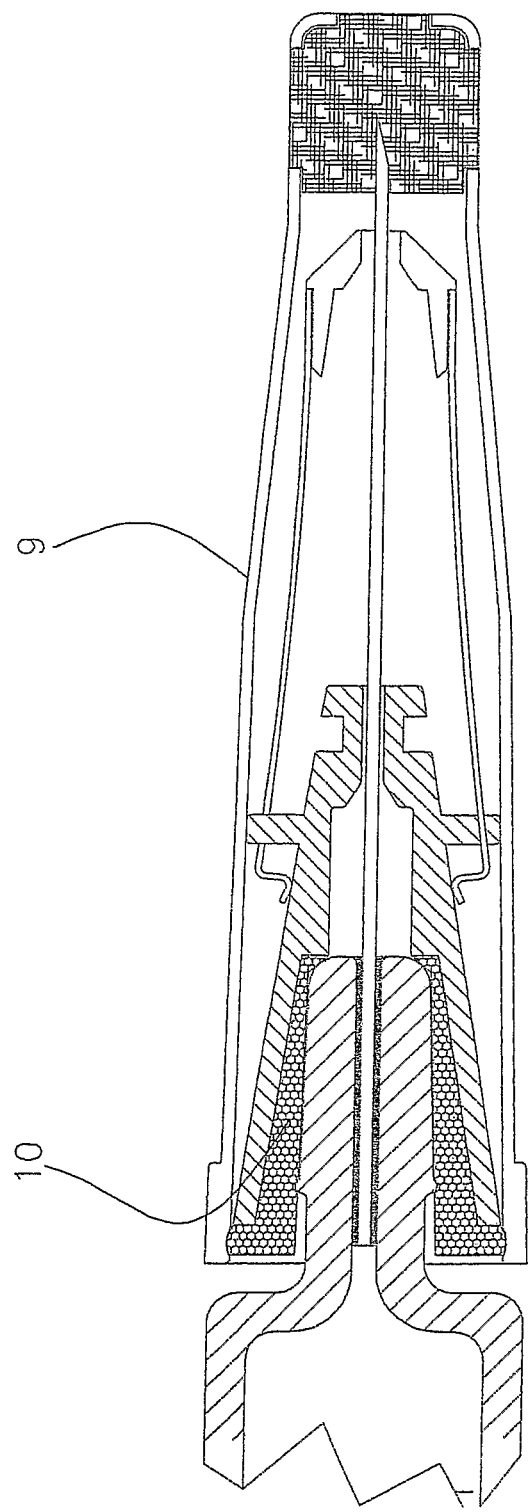
FIG. 4 shows a longitudinal section on the centreline of a syringe and safety needle accessory in accordance with a further embodiment of the present invention.

Unless stated otherwise, like parts are given like notation.

FIG. 1 shows an injection device A having a syringe 1 (only part of the syringe barrel is shown) having a connector 2. Connector 2 has a hole 3, into which is bonded with an adhesive 5 a hollow needle 4 permitting fluid communication between the syringe and the hollow needle 4. The syringe is often made from borosilicate glass, and the stainless steel needle may be bonded with an ultra-violet cured adhesive, this being a typical construction in common use. The safety needle accessory 6, which is more fully described in WO 2004/071560, has a hub 7 which surrounds the connector 2, and is fitted with slidable sleeve 8, although any other safety shield could be used. The sleeve 8, which includes an anterior end 8a and a hindmost end 8b, is arranged to operate when the needle device is pushed onto the patient's skin, by sliding along the hub in the direction of arrow X. When the device is withdrawn from the patient, the sleeve 8 slides back down the hub 7 until it locks in a position to prevent a needle stick injury. There are a number of devices which have been disclosed which achieve the same objective of preventing needle stick injuries, and the present invention may be adapted to suit the features peculiar to those devices, to achieve the same end.

In the present invention, the hub 7 has a hole 14 through which the needle 4 passes with clearance. Hub 7 has an elastic seal 10 which engages sealingly with the connector 2. The connector 2 has a ridge 13 around its circumference, which locally increases the sealing force on the seal 10, and preferably prevents easy removal of the hub 7 and seal 10 from the connector 2. Thus, the elasticity of the seal provides frictional contact between the seal and the other component (here the connector on the syringe) such that a barrier to the ingress of bacteria and pyrogens is created. To achieve low manufacturing cost, the hub 7 may be made from a plastics material, and seal 10 is preferably co-injected molded into the hub 7. This process will ensure bonding of the seal 10 to the hub 7, and thus prevent the passage of harmful bacteria at the junction. Alternatively, and not shown, the seal 10 may be molded as a separate component, and may feature suitable ribs to engage the hub 7. To complete the protection of the drug and needle, a pack 9 is fitted over the safety device/syringe assembly. The pack 9 has an elastic seal 11 which seals onto the rim 15 of seal 10. In addition, a third seal 12 may be located in the closed end of the pack 9, i.e. the end distal to the syringe, and seals the tip of the needle 4. The third seal 12 is typically an elastic seal and sealing is effected by the needle being position such that the tip penetrates the seal 12. The third seal prevents loss or contamination of the injectate. Preferably, the pack 9 has one or more holes 16 sealed by the elastic seal 12, but through which sterilizing gas may permeate. Seal 12 prevents the contents of the syringe 1 from leaking during thermal expansion. The pack 9 is preferably molded in an inexpensive pharmaceutical grade of polyethylene or polypropylene, and the two seals 11 and 12 are preferably co-injection molded to the pack 9. Alternatively, and not shown, both seals 11 and 12 may be made as separate components with the necessary ribs and retaining features to ensure sealing and retention when fitted to the pack 9.

The seal material for the first or second seal 10 and 11 may be low-density polyethylene or a rubber, and the third seal 12 is preferably a pharmaceutical grade of sealing rubber such as iso-butyl rubber. This material is often used because it is a gas-permeable material which permits the passage of a sterilizing gas, such as ethylene oxide, but prevents the passage of harmful bacteria and pyrogens. A common way of bulk packing syringes for pre-filling is to load them into holes in a plastic tray, so that the syringes hang by the finger flange. The loaded tray is placed into a plastic tub, and sealed by a permeable membrane. The sealed tub is subjected to a sterilizing gas such as ethylene oxide, and then, after a period, ordinary atmosphere permeates through the membrane to displace the sterilizing gas, and the membrane prevents the passage of bacteria. During this process, the sterilizing gas also permeates through the rubber seals that protect the needle.

When it is preferable to avoid using ethylene oxide or other sterilizing gas sterilize the assembly, other techniques such as by gamma radiation may be used, and since the sealing materials are not required to be permeable, may be made from other resilient or conformable materials, such as polyester elastomers.

The assembly is shown complete in FIG. 2, and in use, the pack 9 is withdrawn from the syringe/safety needle assembly, FIG. 3, and the injection is given. By incorporating the first and second seals 10 and 11, the ingress of contaminants into the pack 9 is prevented. The first seal 10 provides a seal between the connectors of the syringe 1 and hub 7 when the syringe is attached. The second seal 11 provides a seal between the hub 7 and the interior rim 15 of the open end of the pack 9 when the pack is positioned over the hub 7.

FIG. 4 shows a very similar assembly, but in this case, the first and second seals 10 and 11 are formed of a unitary structure 10' which also seals on the inside of the pack 9, thus reducing the cost of the seals, and reducing the number of potential leakage paths. As an alternative to a unitary structure, the first and second seals are formed separately but are in mutual contact.

Where the accessory is supplied separately from the syringe, the open end of the pack may be covered by a releasable membrane or cap.

Figure 5:
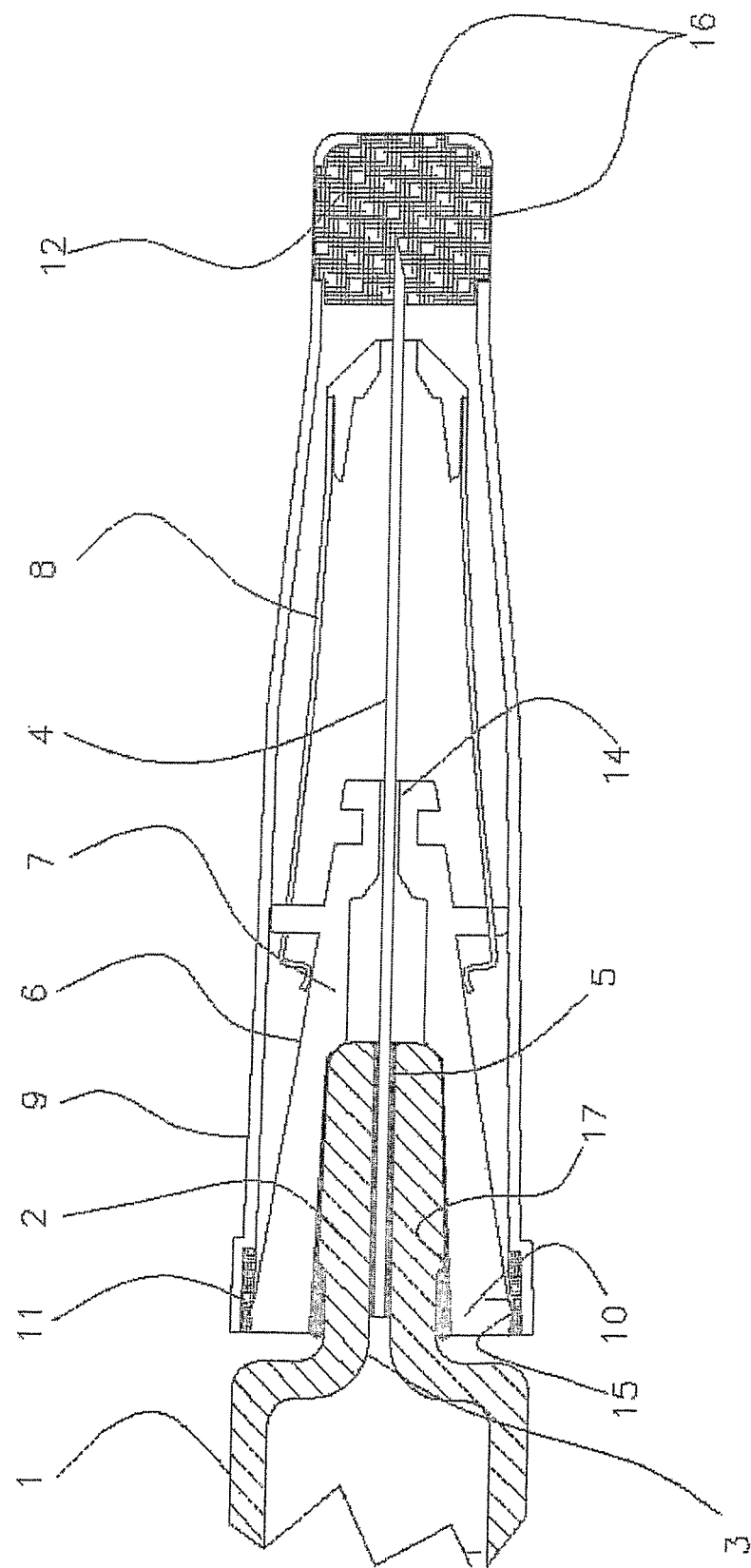
FIG. 5 shows a similar assembly to those illustrated in the other drawings in which the safety device is bonded to the syringe with an adhesive.

FIG. 5 shows yet another alternative method of sealing the hub 7 to the connector 2 by an adhesive 17. Thus, in this embodiment the first seal 10 is an adhesive 17. The adhesive may be coated on the hub 7 and adheres to the syringe when the syringe connector is engaged with the hub connector. Preferably, the injection device is supplied with a pre-filled syringe adhered to the safety needle accessory. A suitable adhesive would be UV-cured or other rapidly setting adhesive compatible with the materials of construction.

The present invention is compatible with current pre-filled syringe technology, including pre-filled reconstitution syringes, whereby a solvent is caused to mix with a lyophilised drug prior to administration.

In all embodiments, when the pack 9 is removed, the safety device remains on the syringe. The present invention is not limited to a precise mechanism of operation of the slidable sleeve. However, the slidable sleeve adapted to slide over the needle in a first longitudinal direction from a first position in which the needle is fully or partially covered by the sleeve to a second position in which the needle is exposed, and in a second longitudinal direction from the second position to a third position in which the needle is fully covered by the sleeve. Preferably the slidable sleeve has an elastically deformable portion 22 and/or further comprises an elastically deformable member 22 such that as the slidable sleeve is caused to move in the first direction towards the second position as the needle is injected into a patient, a resultant force is generated in the deformable portion or deformable member which causes the slidable sleeve to move towards the third (and first) position when the needle is removed from the patient, the safety needle accessory further comprising a locking mechanism 24 capable of retaining the slidable sleeve in the third position after removal of the needle from the patient. The accessory may also further comprise engageable portions 26 on the slidable sleeve and the hub to hold the sleeve in the first position where the sleeve is partially retracted and, when assembled with a syringe having a hollow needle, the needle is partially exposed. This allows the tip of the needle to be seen by the user prior to injection. This assists the user in guiding the needle for placement on the patient's skin or aspirating excess drug or air. Preferably the injection device of the present invention is supplied prior to use with the needle tip partially exposed. The pack is then removed and the needle injected into the patient. Further details are described in WO 2004/071560. Other safety devices intended to prevent or reduce needle-stick injuries, and which may employ a resiliently biased sliding sleeve (see, for example U.S. Pat. No. 4,813,940 and U.S. Pat. No. 5,104,384) may also be used with the accessory of the present invention.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A safety needle accessory comprising:
   a conical hub, having a progressively decreasing diameter from a hindmost end thereof to an anterior end thereof, surrounding both a hollow needle having a tip and a connector of a syringe,
   a slidable sleeve having an anterior end, a hindmost end, and an elastically deformable portion therebetween, wherein:
      the slidable sleeve is slidable along the hub in a first longitudinal direction from a first position, in which the sleeve is partially retracted, such that the needle is partially covered and partially exposed by the sleeve, to a second position, in which the needle is exposed, and in a second longitudinal direction from the second position to a third position, in which the needle is fully covered by the sleeve, and
      as the slidable sleeve is caused to move in the first direction, a resultant force is generated in the deformable portion of the slidable sleeve, to, in turn, cause the slidable sleeve to move in the second direction when the needle is removed from a patient, and
   a pack surrounding the hollow needle, hub and slidable sleeve in the first position, the pack having a closed end covering the needle and an open end,
   wherein the safety needle accessory further comprises a first seal attachable to the connector, a second seal between the hub and the pack configured to provide a seal between the hub and the open end of the pack, and a third seal located in the closed end of the pack and sealing the needle tip in the first position, and wherein at least the second seal and third seal are an elastic seal which is gas-permeable and prevents the passage of bacteria and pyrogens.

2. A safety needle accessory as claimed in claim 1, wherein the first seal is an elastic seal.

3. A safety needle accessory as claimed in claim 1, wherein the closed end of the pack contains one or more holes.

4. A safety needle accessory as claimed in claim 1, wherein the third seal is an iso-butyl rubber.

5. A safety needle accessory as claimed in claim 1, wherein the first and second seals are elastic seals and are in mutual contact.

6. A safety needle accessory as claimed in claim 1, wherein the first and second seals are elastic seals and comprise a unitary structure.

7. A safety needle accessory as claimed in claim 1, wherein the first and second seals are elastic seals and are co-injection molded on to the hub.

8. A safety needle accessory as claimed in claim 1, wherein the first and second seals are composed of one of a low-density polyethylene and a rubber.

9. A safety needle accessory as claimed in claim 1, wherein the first seal is an adhesive.

10. A safety needle accessory as claimed in claim 1, wherein the pack is substantially tubular.

11. A safety needle accessory as claimed in claim 1, further comprising a locking mechanism capable of retaining the slidable sleeve in the third position after removal of the needle from a patient.

12. A safety needle accessory as claimed in claim 1, wherein the needle is partially exposed in the first position.

* * * * *